United States Patent [19]
Miller et al.

[11] Patent Number: 5,944,652
[45] Date of Patent: Aug. 31, 1999

[54] METHOD FOR BREEDING CHICKENS

[75] Inventors: Marcia M. Miller, Altadena, Calif.; Marielle Afanassieff, Le Peage de Roussillon, France; W. Elwood Briles, Sycamore, Ill.

[73] Assignees: City of Hope, Duarte, Calif.; Bd. of Trustees for Nor. Ill. Univ., Dekalb, Ill.

[21] Appl. No.: 08/774,025

[22] Filed: Dec. 27, 1996

[51] Int. Cl.$^6$ .............................. A61B 17/43; A61D 7/00; A01K 29/00; C12P 19/34

[52] U.S. Cl. ........................... 600/33; 119/174; 119/416; 800/8; 435/91.2; 536/24.31; 536/23.53; 424/9.21

[58] Field of Search ................................ 435/91.2, 172.1; 800/2, 8; 536/24.31, 23.53; 119/416, 174; 600/33; 424/9.21

[56] References Cited

U.S. PATENT DOCUMENTS 5,451,670  9/1995  Miller ................................... 536/24.31

OTHER PUBLICATIONS

Kean et al., Poultry Science, vol. 73, pp. 7–17, Jan. 1994.
Wakenell et al., Immunogenetics, vol. 44, pp. 242–245, 1996.
Davidson et al., PCR: A Diagn. Hum. Anim. Virus Dis., pp. 543–552, 1995.
Briles, W.E. et al., Genetics, 35:633–652 (1950).
Pink, J.R.L. et al., Immunogenetics, 5:203 (1977).
Guillemot, F. et al., EMBOJ, 7:2775–85 (1988).
Lamont, S.J. et al., Poult. Sci., 69:1195 (1990).
Shuman, R.M. et al., Development of an Mhc Typing Test Using DNA Amplification and Oligonucleotide Probes, Poult. Sc., 72 (Suppl. 1):10 (Abstr.) (1993).
Miller, M.M. and Goto, R.M., PCR–SSCP: a method for studying the polymorphism of the B–G antigens of the chicken major histocompatibility complex, Avian Immunology in Progress, Tours (France), Aug. 31–Sep. 2, 1993, Ed. INRA, Paris 1993 (Les Colloques, No. 62).
Briles, W.E. et al., A polymorphic system related to but genetically independent of the chicken major histocompatibility complex, Immunogenetics, 37:408–414 (1993).
Miller, M.M. et al., Two Mhc class I and two Mhc class II genes map to the chicken Rfp–Y system outside the B complex, Proc. Nat'l. Acad. Sci. USA, 91:4397–4401 (1994).
Zoorob, R. et al., Eur. J. Immunol., 23:1139–45 (1993).
Afanassiff, M. et al., Abstract presented at the Avian Immunology Research Group Meeting, Obergurgal, Austria, 21–24 Apr. 1996.
Bacon, L.D. and Witter, R.L., Avian Diseases, 36:378–85 (1992).
Bacon, L.D. and Witter, R.L., J. Hered., 86:269–73 (1995).
Wittzell, H. et al., Immunogenetics, 42:68–71 (1995).
Jarvi, S.I. et al., Immunogenetics, 43:125–135 (1996).
Miller, M.M. et al., Proc. Nat'l. Acad. Sci. USA, 93:3958–3962 (1996).
Kroemer, G. et al., Immunogenetics, 31:405–409 (1990).
Blasczyk et al., Complete subtyping of the HLA–A locus by sequence–specific amplification followed by direct sequencing or single–strand conformation polymorphism analysis, Tissue Antigens, 46:86–95 (1995).
Briles, W.E. et al. Animal Genetics, 2:18 (1994).
Schat, K.A. et al., Avian Pathol., 11:593–605 (1982).
Luna, L.G., Manual of Histologic Staining Methods of the Armed Forces Institute of Pathology, 3rd Ed., McGraw–Hill Book Co., New York, pp. 32–46 (1968).

*Primary Examiner*—Deborah Crouch
*Assistant Examiner*—Jill D. Martin
*Attorney, Agent, or Firm*—Rothwell, Figg, Ernst & Kurz

[57] ABSTRACT

Disease resistance in chickens has been associated with the Rfp-Y system of major histocompatability genes in chickens. A method for breeding chickens to produce disease resistant offspring involves selecting at least one parent that has an Rfp-Y haplotype that is characteristic of disease resistance and mating that parent with a second parent to produce a disease resistant offspring.

3 Claims, No Drawings

METHOD FOR BREEDING CHICKENS

This invention was funded in part by the United States Department of Agriculture under Federal Assistance Program Agreement No. 58-3148-5-023 and NRICGP 92-37204-8244. The U.S. government may have certain rights in the invention.

BACKGROUND OF THE INVENTION

1. Field of the Invention

This invention relates to a method for breeding domesticated fowl for increased disease resistance. In a particular aspect, the invention relates to a method for breeding chickens raised for meat and eggs to achieve increased disease resistance. In a further related aspect, the invention relates to a method for determining the Rfp-Y of B-F haplotype of domesticated fowl, including chickens.

2. Description of the Background Art

In domesticated fowl, the major histocompatibility complex ("Mhc") which is associated with the regulation of immune recognition and immune response, is called the B system. This system, which comprises polymorphic Mhc class I, class II and B-G genes, has been known to exist since the early 1940's. Briles, W. E. et al., *Genetics*, 35:633–652 (1950), Pink, J. R. L. et al., *Immunogenetics*, 5:203 (1977). U.S. Pat. No. 5,451,670 to Miller, M. M. et al. describes a procedure for determining the genotype of the B-G region of the Mhc. Cosmid cluster I on the molecular map of the chicken Mhc genes published by Guillemot, F. et al., *EMBO J*, 7:2775–85 (1988) corresponds to the B system. Resistance to Marek's disease and other diseases, general fitness and productivity have been associated with the B system haplotype.

Genotyping birds for the B system of histocompatibility can be accomplished by five different kinds of tests. The first, and by far the most commonly used method, is a serological test: hemagglutination of chicken red blood cells with alloantisera. This method requires some prior knowledge of the genetics of the animals and availability of appropriate alloantisera. The second relies on the patterns of B-G gene restriction fragments revealed in genomic DNA digested with a restriction enzyme and analyzed in Southern hybridization with nucleic acid probes for the B-G genes. See Miller, M. M., U.S. Pat. No. 5,451,670. An advantage of this approach is that prior knowledge of gene sequences is not necessary. A third method relies on B-F (class I) and B-L (class II) gene restriction fragment patterns revealed in genomic DNA digested with several restriction enzymes and analyzed by Southern hybridization with nucleic acid probes for the B-F and B-L genes. See Lamont, S. J. et al., *Poult. Sci.*, 69:1195 (1990). A fourth method is based on hybridization of oligonucleotide probes specific for known sequences in the various alleles of the B system class I gene (gene B-FIV on the physical map of chicken Mhc genes (See Guillemot, F. et al., 1988, supra.)). This method requires knowledge of the sequence of the allele at least in the region to which the probe hybridizes. See Shuman, R. M. et al., "Development of an Mhc Typing Test Using DNA Amplification and Oligonuleotide Probes", *Poult. Sci.*, 72 (Suppl. 1): 10 (Abstr.) (1993). A fifth method employs antibodies developed to a specific epitope on class I antigens through expression of recombinant genes in chickens.

The use of a technique known as polymerase chain reaction, single-stranded conformational polymorphism ("PCR-SSCP") to study the expression of B-G genes in non-erythroid tissues has been proposed. Miller, M. M. and Goto, R. M., *Avian Immunology in Progress*, Tours (France), Aug. 31–Sep. 2, 1993, Ed. INRA, Paris 1993 (Les Colloques, No. 62). In this method, short segments of B-G genes of interest are amplified using PCR. The PCR products are then denatured by heating and applied to a non-denaturing polyacrylamide gel. The single-stranded fragments of the heat-denatured DNA fragments assume secondary conformations determined by their sequences and migrate differently in the polyacrylamide gel during electrophoresis, so as to produce a pattern (or fingerprint) representative of the sequences within the genome in the region of amplification.

Recently, a second system of major histocompatibility genes of the chicken has been discovered. Briles, W. E. et al., *Immunogenetics*, 37:408–414 (1993). This system, designated Rfp-Y, consists of at least two class I genes, three class II genes and a c-type lectin gene. Miller, M. M. et al., *Proc. Nat'l. Acad. Sci. USA*, 91:4397–4401 (1994). Haplotypes of Rfp-Y assort independently from haplotypes of the B system. Briles, W. E. et al. (1993), supra.

The existence of a second genetically-independent complex of polymorphic histocompatibility genes was unexpected, because Mhc genes are typically considered to be in a single linkage group. Previous studies have suggested that at least one Mhc class II gene in the B-L βIII gene family, now known to be within Rfp-Y is expressed. Zoorob, R. et al., *Eur. J. Immunol.*, 23:1139–45 (1993). Transcripts of an Mhc class I gene within Rfp-Y were also found in many different tissues. See Afanassiff, M. et al., Abstract presented at the Avian Immunology Research Group Meeting, Obergurgal, Austria, Apr. 21–24, 1996. Nevertheless, the role of the Rfp-Y system in immune mediation of disease resistance and the extent to which genes of the Rfp-Y system are expressed in various cell types has heretofore remained unknown.

SUMMARY OF THE INVENTION

In accordance with the present invention, it has been discovered that the Rfp-Y system exerts an effect on Marek's disease resistance. It has also been discovered that, in some allelic combinations, the influence of the Rfp-Y and B systems on Marek's disease resistance may be additive. Accordingly, a method for breeding domesticated fowl to produce disease-resistant offspring comprises selecting at least one parent that has an Rfp-Y haplotype that is characteristic of disease resistance and mating that parent with a second parent to produce a disease resistant offspring.

The invention also provides a method for determining the haplotype of Rfp-Y or B-F genes of a domesticated fowl, which comprises:

(a) obtaining a sample of nucleic acid which contains a region having a sequence corresponding to that of an Rfp-Y or B-F region of the genome of said domesticated fowl which is subject to alielic variation;

(b) amplifying said region to produce amplification products;

(c) denaturing said amplification products to produce denatured amplification products;

(d) subjecting said denatured amplification products to non-denaturing electrophoretic separation to produce an electrophoresis pattern that is characteristic of the Rfp-Y or B-F class I haplotype of said domesticated fowl.

DETAILED DESCRIPTION OF THE INVENTION

Breeding programs for domesticated fowl typically are designed to breed disease resistance, as well as numerous other advantageous characteristics, into commercial lines. Marek's disease is of particular interest, in that it is a disease of chickens encountered worldwide. Virtually all commercially grown chickens (there are about thirty-four billion broiler chickens raised annually worldwide) are vaccinated for Marek's disease.

The experimental data described herein indicate that resistance to Marek's disease is influenced by the Rfp-Y haplotype as well as the B system haplotype. Pedigree-hatched chicks in families from stock in which three Rfp-Y haplotypes and two B system haplotypes were segregating were challenged with Marek's disease virus ("MDV"). The resulting data demonstrated that both the Rfp-Y and B haplotypes significantly influence the outcome of infection with MDV. Moreover, vaccines are only partially effective, and their effectiveness is also influenced by the B genotype (Bacon, L. D. and Witter, R. L., *Avian Diseases*, 36:378–85 (1992) and Bacon, L. D. and Witter, R. L., J. Hered., 86:269–73 (1995)) and, probably to some degree, the Rfp-Y genotype of the birds.

Thus, determining the Rfp-Y haplotype of domesticated fowl can facilitate breeding programs in which it is desired to breed resistance to Marek's disease and other diseases that are influenced by the Mhc into birds raised for meat or eggs. Rfp-Y haplotyping can be accomplished by a variety of procedures, including restriction fragment length polymorphism ("PFLP"), cDNA cloning followed by sequencing, allele-specific oligonucleotide probing and the like. To be used effectively in a breeding program, the haplotyping method should be relatively simple, reliable and fast so that large numbers of samples can be processed quickly and efficiently. A preferred method that meets these requirements is the nucleic acid amplification-SSCP method described below.

To utilize Rfp-Y haplotyping in a commercial breeding program, a database correlating Rfp-Y haplotypes to Marek's or other disease resistance in known breeding lines is created. Breeders can then utilize this database, in conjunction with information about B system Mhc haplotype and other characteristics, in selecting parents. The breeding and haplotyping methods described herein may be used in connection with any species of domesticated fowl that possesses an Rfp-Y Mhc system. The methods are preferably used in breeding programs for domesticated chickens. Evidence of an Rfp-Y system in ring-necked pheasants has been reported. See Wittzell, H. et al., *Immunogenetics*, 42:68–71 (1995) and Jarvi, S. I. et al., *Immunogenetics*, 43:125–135 (1996). Data also exists which suggests the presence of an Rfp-Y system in turkeys.

The Rfp-Y region is believed to reside on chicken chromosome 16 (a microchromosome), which also contains the Mhc B region. A genetic map can be postulated for chicken chromosome 16, showing the Rfp-Y system, encompassing two Mhc class I genes and three Mhc class II genes, separated from the B system by a region containing the nucleolar organizer region ("NOR"). See Miller, M. M. et al., *Proc. Nat'l. Acad. Sci. USA*, 93:3958–3962 (1996).

The nucleic acid amplification-SSCP haplotyping method of this invention involves amplifying a segment of DNA spanning an allelic region of the Rfp-Y system or the B-F system. The amplification procedure used may be any method that specifically amplifies the nucleic acid of interest, including polymerase chain reaction ("PCR"), ligase chain reaction, nucleic acid specific base amplification ("NASBA"), and the like. PCR is the preferred amplification procedure.

Genomic DNA, mRNA or cDNA containing a nucleic acid sequence corresponding to the Rfp-Y or B-F region to be amplified may be used as the sample for the amplification reaction. A genomic DNA sample is preferred.

The segment to be amplified is selected to include one or more allelic regions, so as to produce a unique electrophoretic pattern when subjected to the SSCP procedure. The segment advantageously ranges from about 50 to about 500 nucleotides in length, preferably from about 100 to about 300 nucleotides. Those skilled in the art will recognize that a variety of segments may be selected for amplification.

To be of value in typing for the B and Rfp-Y systems, the segments chosen should be specific for one system or the other so as not to produce patterns from both systems that cannot be distinguished in the electrophoretic patterns. To obtain this specificity, primer sets are chosen that are specific for either the B or the Rfp-Y class I loci. The two primer sets are chosen so that they span a region expected to be polymorphic in these loci. For example, the primer set chosen for the B system advantageously hybridizes with sequences within both class I genes of the B system. In this way if either one or both loci are polymorphic in a particular haplotype the primers will produce DNA amplification products that will provide distinctive electrophoretic patterns. Both class II β-chain and the class I α-chain genes within the Rfp-Y and the B systems are useful for this approach; however, the class I genes have been found to be especially appropriate for the tests disclosed herein.

Amplification primers are selected from the sequences of the Rfp-Y and B system class I genes. The two class I genes of the Rfp-Y system (designated Y-FV and Y-FVI) and the two class I genes of the B-F region (designated B-FIV and B-FI) are contained within the cosmids described by Guillemot, F. et al. (1988) supra and are identified on the molecular map of the chicken Mhc genes published by those authors. The sequence of the B-FIV gene has been published. Kroemer, G. et al., *Immunogenetics*, 31:405–409 (1990). Sequences of other Rfp-Y and B genes contained within the cosmids can be determined by standard procedures. Primers should be specific for each system to allow the amplification of the genes within only one system, Rfp-Y or B.

Following amplification, the amplification products are subjected to single-stranded conformational polymorphism ("SSCP") electrophoretic separation. SSCP has been described in connection with other Mhc genes. See Blasczyk et al., *Tissue Antigens*, 46:86–95 (1995).

The amplification products first are denatured to form single-stranded molecules. Chemical denaturation, e.g., with formamide, heat denaturation or enzymatic denaturation can be employed.

The denatured single-stranded amplification products are then separated electrophoretically under non-denaturing conditions. Preferably, the electrophoresis is conducted on a non-denaturing polyacrylamide gel, such as a 10% polyacrylamide buffered with tris-borate EDTA (TEE). Under these conditions, the single-stranded molecules assume conformations that are affected by the nucleotide sequences. It has been found that a difference in a single base can affect conformation sufficiently that an electrophoretic separation can be achieved.

The amplification products may be visualized on the gel by any appropriate method, such as silver staining, ethidium bromide staining or Sybr™ green I nucleic acid stain available from Molecular Probes, Inc., Eugene, Oreg. 97402-0414 USA. Silver staining is preferred.

The nucleic acid amplification-SSCP procedures are fast and convenient and have been found to produce patterns characteristic of Rfp-Y and B-F gene haplotypes. As these patterns are developed for a wide range of commercial lines, a database will be created that will allow breeders to select birds for breeding which have Rfp-Y and/or B-F haplotypes that are associated with resistance to Marek's and other diseases.

The invention is further illustrated by the following examples, which are not intended to be limiting.

EXAMPLE I
(Correlation of Rfp-Y Haplotype and Marek' Disease Resistance)

Chickens. Chicks used in the challenge experiments were produced by parents from the stock in which the Rfp-Y system had been originally identified (Briles, W. E. et al. (1993) supra). B system haplotypes segregating in the stock were $B^{11}$ and $B^{19}$. The $R^{R9}$ haplotype ($B^{24r2}$ by standard international nomenclature) is one of the 12 B-F/B-G recombinant haplotypes preserved at Northern Illinois University, designated as $B^{R1}$ through $B^{R12}$. Typing with B-F and B-G specific alloantisera showed that $B^{R9}$ consists of $F^{24}$-$G^{23}$ (Briles, W. E. et al., Animal Genetics, 25(supplement 2):18 (1994)) with further evidence for B-$G^{23}$ found in the analysis of B-G proteins by two dimensional gel electrophoresis (Miller, M. M. et al. 1988).

B system genotypes among parents. Matings for the production of chicks to be challenged with MDV were designed so that each family would be expected to consist of $B^{11}/B^{11}$ and $B^{R9}/B^{11}$ genotypes in an expected 1:1 ratio. The chicks resulted from the mating of three sires of genotype $B^{R9}/B^{11}$ to seven females of the genotype $B^{11}/B^{11}$ and of six males of genotype $B^{11}/B^{11}$ to fifteen females of the genotype $B^{R9}/B^{11}$.

Rfp-Y system genotypes among parents. The primary objective in designing the matings to produce chicks for challenge with MDV was to obtain from each individual mating two Y genotypes among the progeny—a homozygote and a heterozygote having one allele in common. For example, a male of the genotype $Y^3/Y^3$ mated to a female of the genotype $Y^1/Y^3$ would be expected to produce progeny of the genotypes $Y^1/Y^3$ and $Y^3/Y^3$. The requirement that each mating be designated to produce in equal numbers of two Y genotypes was instituted to reduce the confounding of Y genotype performance of the challenged chicks with family structure. The gene frequencies for the $Y^1$, $Y^2$ and $Y^3$ among the 22 females were 0.39, 0.27, and 0.34, respectively, and among the 9 males were 0.17, 0.11, and 0.72, respectively. In addition to the restrictions regarding distribution of B and Rfp-Y among the parents, each male and female paired to produce chicks were from different families of the previous year.

Challenge of chicks with MDV. Matings were made by artificial insemination, eggs were labeled by mating code and shipped to the University of California at Davis by overnight freight for incubation and pedigree hatch. The chicks were double wing-banded to avoid accidental loss of identity and were reared on the floor in a clean environment. Feed and water were available ad libitum, and the chicks were observed at least once daily. Specific pathogen-free (SPF) eggs were obtained from flock RF2 maintained at HyVac Inc., Ames, Iowa, incubated, and hatched at the University of California at Davis. The chicks were placed unbanded in rooms with the chicks hatched from the experimental matings.

Virus and inoculation procedures. The pedigree-hatched chicks were challenged intra-abdominally with 500 plaque forming units of the RB1B strain of MDV (Schat, K. A. et al. Avian Pathol., 11:593–605 (1982)). The RB1B virus was propagated in chick-kidney tissue culture cells at the University of California at Davis. The virus from the third or fourth passage was used for challenge. All SPF chicks received their challenge by contact-exposure to the intra-abdominally challenged chicks.

Blood collection and testing. Whole blood samples were collected in EDTA collection tubes and were analyzed for the B and Rfp-Y haplotypes of the individual birds. The haplotypes were determined by restriction fragment patterns displayed in Southern hybridizations of DNA digested with Bgl I restriction enzyme and hybridized with a B-LBII probe, as previously described (Briles, W. E. et al. (1993) supra. B types were distinguished by the presence of restriction fragments of approximately 4.0 and 4.4 kb.

Tissue collection and processing. Chicks were euthanized and the thymus, spleen, liver, kidney, lung, gonads, sciatic nerves and plexes, brachial nerves and plexes, bursa of Fabricius, heart, and any other affected tissues were collected for histological processing. Tissues were fixed in 10% neutral buffered formalin, imbedded in paraffin, sectioned at 6 um, and stained with hematoxylin and eosin (Luna, L. G., Manual of Histologic Staining Methods of the Armed Forces Institute of Pathology, 3rd Ed., McGraw-Hill Book Co., New York, pp. 32–46 (1968)).

Experimental design. Replicate trials were conducted as follows: Trial 1: Incubation of two hundred pedigreed eggs resulted in 97 chicks; 86 of which completed the challenge test. At 5 days of age, the chicks were challenged and 10 one-day-old SPF chicks were added to the flock. Chicks were observed daily for clinical signs of Marek's disease ("MD") and post-mortem examinations were conducted on all dead birds. At 3 weeks of age, blood samples were collected for B and Y typing of individual chicks. The trial was terminated 75 days post-challenge (PC) and a gross necropsy examination was performed on all birds. Tissues were collected from all birds dying prior to termination and at termination for confirmation of MD by microscopic examination. In trial 1 seven out of 8 SPF control birds had gross and/or histologic evidence for MDV tumor formation.

Trial 2: Incubation of two hundred pedigreed eggs resulted in 87 chicks; 80 of which completed the challenge test. Challenge, blood collection, and handling were conducted as in Trial 1. Four SPF chicks were added to the flock on day 4 PC. The trial was terminated on day 75 PC. In trial 2 four out of four SPF control chicks had gross and/or histologic evidence of MDV tumor formation.

Statistical analysis. Logistic regression was used to investigate the joint dependence of tumor incidence on genotypes at both the B and Rfp-y systems. For the B system, a single dummy variable was created, parameterizing the risk in $B^{R9}/B^{11}$ homozygotes. For the Rfp-Y system, the effect of the $Y^3$ haplotype was explored, because this is the most frequently occurring Rfp-Y haplotype in this genetic stock in which Rfp-Y was first recognized. This stock is several generations into the production of congenic lines for B system recombinant haplotypes and was otherwise without selection. Three models were compared for the effect of the $Y^3$ haplotype, denoted dominant, recessive and codominant. In the dominant model, $Y^3$ homozygotes and heterozygotes were combined and their risk estimated relative to non-$Y^3$ carriers. In the recessive model, $Y^3$ homozygotes are compared with the remaining birds, and in the codominant model, the risks for $Y^3$ homozygotes and heterozygotes were separately estimated, relative to non-$Y^3$ carriers. Likelihood ratio tests and Akaike's Information Criteria (AIC) were used to compare alternative models.

Results. Overall, MD was observed in 51 (30%) of the 168 birds on study. Table 1 shows the distribution of MD tumors tabulated by genotypes at the B and Rfp-Y systems. There was significantly higher incidence in $B^{R9}/B^{11}$ birds (39.4%), compared with $B^{11}/B^{11}$ birds (23.7%, P=0.029), collapsing across Rfp-Y genotypes. The frequency of birds with respect to Rfp-Y genotypes shows that 37% of the birds are homozygous for $Y^3$, 40% are heterozygous for $Y^3$ and only 33% carry one of the remaining three genotypes. Incidence rates range from 18% for $Y^2/Y^3$ carriers to 43% for $Y^1/Y^2$ carriers, although the latter estimate is based on only seven birds. With respect to the $Y^3$ haplotype, the highest incidence is observed for $Y^3/Y^3$ homozygotes (40%).

Based on the logistic regression analysis, the B system was significantly associated with tumor incidence (P<0.02), regardless of the type of model used for the Rfp-Y system. Conditional on the B system included in the model, the recessive model for $Y^3$ fit the data better than the dominant or the codominant model, with $Y^3/Y^3$ homozygotes showing significantly higher incidence than birds with other genotypes combined (P<0.02). Additionally this model also predicts incidence for $B^{R9}/B^{11}$ heterozygotes to be 2.3 times higher than the incidence for $B^{11}/B^{11}$ homozygotes. In a subsequent analysis, a term was added to the model for the interaction between the B system and the recessively coded Rfp-Y system. This interaction was not found to be statistically significant (P=0.89).

(Mallinckrodt). Thirty cycles of PCR were performed with each cycle consisting of denaturation for 45 seconds at 95° C., annealing for 45 seconds at 63° C. and elongation for 45 seconds at 72° C., followed by one cycle of PCR with elongation for 5 minutes at 72° C.

The PCR reaction was monitored by agarose gel electrophoresis as follows: A 1.5% agarose (FMC Bioproducts) electrophoresis gel in tris-borate EDTA ("TBE") 1× buffer (89 mM Tris-borate (Fisher Biotech), 89 mM boric acid (Mallinckrodt) and 2 mM EDTA (Mallinckrodt)) was prepared. Five to ten microliters of PCR products were loaded onto the gel with 1 μl dye 10× (0.5% bromophenol blue (Sigma), 0.5% Xylene cyanol (Gibco-BRL), 40% (w/v) sucrose (IBI) in water). Electrophoresis was run in TBE 1× at 120 V for 45 minutes. The gel was stained with ethidium bromide (10 μg/ml, Sigma) for 5 minutes. PCR products were visualized with ultraviolet light.

SSCP electrophoresis of the PCR products was conducted as follows:

A 10% polyacrylamide gel in TBE (0.5×) was prepared by combining (for a 6 ml gel) 3.7 ml water, 300 μl TBE 10×, 2 ml acrylamide (11.4 g acrylamide (Boehringer) plus 0.6 g bis-acrylamide (BioRad) in 40 ml water), 3 μl TEMED (N,N,N',N'-tetramethylethylenediamine) (Sigma) and 30 μl ammonium persulfate 10% (BioRad).

PCR products (1 to 3 μl) were denatured for 5 minutes at 80° C. with 10 μl dye 1× (300 μl formamide (Fisher) plus 3

TABLE 1

Incidence of Marek's Disease Tumors by Rfp-Y and B Genotype

| B Genotype | 1/1 | 1/2 | 1/3 | Rfp-Y 2/2 | Genotype 2/3 | 3/3 | Combined |
|---|---|---|---|---|---|---|---|
| $B^{11}/B^{11}$ | 13%(1/8) | 40%(2/5) | 11%(2/18) | 0%(0/5) | 23%(5/22) | 33%(13/39) | 24%(23/97) |
| $B^{R9}/B^{11}$ | 38%(3/8) | 50%(1/2) | 50%(8/16) | 40%(2/5) | 12%(2/17) | 52%(12/23) | 39%(28/71) |
| Combined | 25%(4/16) | 43%(3/7) | 29%(10/34) | 20%(2/10) | 18%(7/39) | 40%(25/62) | 30%(51/168) |

EXAMPLE II
(PCR-SSCP Determination of Rfp-Y and B-F Haplotypes)

The PCR-SSCP typing tests are based on sequences coding for the α1 domains of class I molecules, B-FI, B-FIV, Y-FV and Y-FVI identified as SEQ. ID NO. 1, SEQ. ID NO. 2, SEQ ID NO. 3 and SEQ ID NO. 4 respectively. Two primer sets were used. Primers 72 and 73, the primers for the sense and antisense strands of the B-F gene segments, are identified in SEQ ID NO. 5 and SEQ ID NO. 6, respectively. Primers 75 and 76, the primers for the sense and antisense strands of Y-F gene segments, are identified in SEQ ID NO. 7 and SEQ ID NO. 8, respectively. The sequences are set forth in the Sequence Listing.

The conditions for PCR amplification of these 174 base pair segments were as follows:

PCP reaction mixture:

5 μl of Taq. DNA Polymerase Buffer 10× (Perkin Elmer Corp.)

1 μl dNTP mixture (dATP, dCTP, dGTP, dTTP, 10 mM each, Boehringer)

1 μl primer 72 or 75 (20 μM)

1 μl primer 73 or 76 (20 μM)

100 ng genomic DNA qsp 49 μl with water.

Samples were denatured for 5 minutes at 95° C. and were conserved on ice. One microliter (1 U) of Taq DNA polymerase diluted 5× (Perkin Elmer 5 U/μl) was added and the samples were covered with 30 μl of white mineral oil μl dye 10×). The denatured PCR products were loaded onto the gel. Electrophoresis was run in TBE 0.5× at 200 V for 1 hour 45 minutes. The gel was fixed by treating for 20 minutes with 50 ml. of: methanol 50% (v/v) (Mallinckrodt), acetic acid 10% (v/v) (Mallinckrodt), fixative enhancer concentrate 10% (v/v) (BioRad Silver Stain Plus Kit) in water 30% (v/v). The fixed gel was washed twice with water for 10 minutes. A staining solution (BioRad Silver Stain Plus Kit) was prepared by combining the following: 25 ml water, 2.5 ml Silver Complex Solution, 2.5 ml Reaction Moderator Solution, 2.5 ml Image Development Reagent and 12.5 ml Development Accelerator Solution. The gel was stained with this solution for 10 minutes, was fixed with 25 ml 5% acetic acid for 15 minutes and was dried in cellophane.

The PCR reaction yielded products of the expected size (174 bp). The resulting SSCP patterns for seven B system haplotypes, $B^Q$, $B^2$, $B^{12}$, $B^{15}$, $B^{18}$, $B^{21}$ and $B^{24}$, and nine Rfp-Y haplotypes, $Y^1$ to $Y^9$, are shown in FIGS. 1–4. A 174 bp non-denatured PCR amplification product is shown in the first lane at the left of the figure. After denaturation, electrophoresis and staining, these PCR amplification products give different patterns of bands which are specific for the sequences amplified and consequently specific for the haplotype from which they originate. B system patterns produced with primers 72 and 73 are presented on the gel to the left and Rfp-Y systems patterns produced with primers 75 and 76 are presented on the gel to the right. Thus, the PCR-SSCP method provides a fast and efficient means for determining the Rfp-Y and B-F haplotypes.

We claim:

1. A method for breeding chickens to produce offspring, which comprises selecting at least one parent that has an Rfp-Y haplotype that correlates with reduced incidence of tumor formation upon exposure to Marek's disease virus and mating said parent with a second parent to produce offspring, wherein the offspring demonstrate reduced incidence of tumor formation upon exposure to Marek's disease virus.

2. The method of claim 1, wherein both parents are selected to have an Rfp-Y haplotype that correlates with said reduced incidence of tumor formation upon exposure to Marek's disease virus.

3. The method of claim 1, comprising further selecting said at least one parent on the basis of a B system haplotype that correlates with said reduced incidence of tumor formation upon exposure to Marek's disease virus.

* * * * *

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
        (A) LENGTH: 264 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Gallus domesticus (xi) SEQUENCE DESCRIPTION: SEQ ID NO:1:

AGCTCCATTC CCTGCGGTAC GTCCATACGG CGATGACGGA TCCCGGCCCC GGGCTGCCGT     60

GGTTCGTGGA CGTGGGGTAC GTGGACGGGG AACTCTTCGT GCACTACAAC AGCACCGCGC    120

GGAGGTACGT GCCCCGCACC GAGTGGATGG CGGCCAACAC GGACCAGCAG TACTGGGATG    180

GACAGACGCA GATCGGACAG GGCAATGAGC GGAGTGTGGA AGTGAGCTTG AACACACTGC    240

AGGAACGATA CAACCAGACC GGCG                                          264

(2) INFORMATION FOR SEQ ID NO:2:

(i) SEQUENCE CHARACTERISTICS:
        (A) LENGTH: 264 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Gallus domesticus (xi) SEQUENCE DESCRIPTION: SEQ ID NO:2:

AGCTCCATAC CCTGCGGTAC ATCCAAACGG CGATGACGGA TCCCGGCCCC GGGCAGCCGT     60

GGTTCGTGAC TGTGGGGTAC GTGGACGGGG AACTCTTCGT GCACTACAAC AGCACCGCGC    120

GGAGGTACGT GCCCCGCACC GAGTGGATAG CGGCCAAGGC GGACCAGCAG TACTGGGATG    180

GACAGACGCA GATCGGACAG GGCAATGAGC AGATTGACCG CGAGAACCTG GCATACTGC     240

AGCGGCGCTA CAACCAGACC GGCG                                          264

(2) INFORMATION FOR SEQ ID NO:3:

(i) SEQUENCE CHARACTERISTICS:
        (A) LENGTH: 261 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Gallus domesticus (xi) SEQUENCE DESCRIPTION: SEQ ID NO:3:

GGTCGCACTC CCTGCGCTAC TTCCTGACCG GGATGACGGA TCCCGGCCCC GGGATGCCGC      60

GGTTCGTGAT CGTCGGGTAC GTGGACGACA AAATCTTCGG TACCTACAAC AGTAAGAGCA    120

GGACTGCACA GCCTATCGTG GAGATGCTGC CGCAGGAGGA CCAGGAGCAC TGGGACACGC    180

AGACCCAGAA GGCGCAGGGC GGTGAGCGGG ATTTTGACTG GAACCTGAAC AGGCTGCCGG    240

AACGCTACAA CAAAAGTAAA G                                              261

(2) INFORMATION FOR SEQ ID NO:4:

(i) SEQUENCE CHARACTERISTICS:
        (A) LENGTH: 261 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Gallus domesticus (xi) SEQUENCE DESCRIPTION: SEQ ID NO:4:

GGTCGCACTC CCTGCGCTAC TTCCTGACCG GGATGACGGA TCCCGGCCCC GGGATGCCGC      60

GGTTCGTGAT CGTCGGGTAC GTGGACGACA AAATCTTCGG TATCTACGAC AGTAAGAGCA    120

GGACTGCACA GCCCATCGTG GAGATGCTGC CGCAGGAGGA CCAGGAGCAC TGGGACGCGC    180

AGACCCAGAA GGCCCAGGGC GGTGAGCGGG ATTTTGACTG GTTCCTGAGC AGGCTGCCGG    240

AACGCTACAA CAAAAGTGGA G                                              261

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Gallus domesticus (xi) SEQUENCE DESCRIPTION: SEQ ID NO:5:

GACGGGGAAC TCTTCGTGCA                                                  20

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

```
        (iii) HYPOTHETICAL: NO (iv) ANTI-SENSE: YES (vi) ORIGINAL SOURCE:
              (A) ORGANISM: Gallus domesticus (xi) SEQUENCE DESCRIPTION: SEQ ID NO:6:

TCTGGTTGTA GCGCCGCTGC A                                                 21

(2) INFORMATION FOR SEQ ID NO:7:

(i) SEQUENCE CHARACTERISTICS:
              (A) LENGTH: 22 base pairs
              (B) TYPE: nucleic acid
              (C) STRANDEDNESS: single
              (D) TOPOLOGY: linear (ii) MOLECULE TYPE: DNA (genomic)

(iii) HYPOTHETICAL: NO (iv) ANTI-SENSE: NO (vi) ORIGINAL SOURCE:
              (A) ORGANISM: Gallus domesticus (xi) SEQUENCE DESCRIPTION: SEQ ID NO:7:

GTGGACGACA AAATCTTCGG TA                                                22

(2) INFORMATION FOR SEQ ID NO:8:

(i) SEQUENCE CHARACTERISTICS:
              (A) LENGTH: 23 base pairs
              (B) TYPE: nucleic acid
              (C) STRANDEDNESS: single
              (D) TOPOLOGY: linear (ii) MOLECULE TYPE: DNA (genomic)

(iii) HYPOTHETICAL: NO (iv) ANTI-SENSE: YES (vi) ORIGINAL SOURCE:
              (A) ORGANISM: Gallus domesticus (xi) SEQUENCE DESCRIPTION: SEQ ID NO:8:

TTTGTTGTAG CGTTCCGGCA GCC                                               23
```